US006423100B1

(12) United States Patent
Lang et al.

(10) Patent No.: US 6,423,100 B1
(45) Date of Patent: *Jul. 23, 2002

(54) COMPOSITION FOR OXIDATION DYEING OF KERATIN FIBERS AND PROCESS USING SAME

(75) Inventors: Gèrard Lang, Saint Prix; Jean Cotteret, Verneuil sur Seine, both of (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/331,323

(22) PCT Filed: Oct. 16, 1998

(86) PCT No.: PCT/FR98/02231

§ 371 (c)(1),
(2), (4) Date: Aug. 30, 1999

(87) PCT Pub. No.: WO99/20236

PCT Pub. Date: Apr. 29, 1999

(30) Foreign Application Priority Data

Oct. 22, 1997 (FR) .............................. 97-13243

(51) Int. Cl.$^7$ ................................. A61K 7/13
(52) U.S. Cl. ................ 8/401; 8/406; 8/409; 8/416; 8/421; 8/423; 8/424
(58) Field of Search ......................... 8/406, 409, 416, 8/421, 423, 424, 401

(56) References Cited

U.S. PATENT DOCUMENTS

| 3,251,741 | A | * | 5/1966 | Soloway | |
|---|---|---|---|---|---|
| 4,961,925 | A | * | 10/1990 | Tsujino et al. | 8/406 |
| 5,538,517 | A | * | 7/1996 | Samain et al. | 8/423 |
| 5,833,969 | A | * | 11/1998 | Tsujino et al. | 424/70.122 |
| 5,849,041 | A | | 12/1998 | Kunz et al. | 8/408 |
| 6,004,355 | A | * | 12/1999 | Dias et al. | 8/401 |
| 6,022,381 | A | * | 2/2000 | Dias et al. | 8/401 |
| 6,027,719 | A | * | 2/2000 | Tomura et al. | 424/78.02 |

FOREIGN PATENT DOCUMENTS

| EP | 0 310 675 | | 4/1989 |
|---|---|---|---|
| EP | 0 716 846 | | 6/1996 |
| EP | 0 795 313 | | 9/1997 |
| FR | 2 586 913 | | 3/1987 |
| WO | WO 97/37633 | | 10/1997 |
| WO | 98/22078 | * | 5/1998 |

OTHER PUBLICATIONS

English language Derwent Abstract of FR 2 586 913, Mar. 1987.

* cited by examiner

*Primary Examiner*—Margaret Einsmann
(74) *Attorney, Agent, or Firm*—Finnegan, Henderson, Farabow, Garrett & Dunner, LLP

(57) ABSTRACT

The invention relates to a ready-to-use composition for the oxidation dyeing of keratin fibers, and in particular human keratin fibers such as the hair, comprising, in a medium which is suitable for dyeing, at least one self-oxidizing dye, and at least one enzyme of 2-electron oxidoreductase, type, in the presence of at least one donor for the said enzyme, as well as to the dyeing process using this composition.

41 Claims, No Drawings

COMPOSITION FOR OXIDATION DYEING OF KERATIN FIBERS AND PROCESS USING SAME

The invention relates to a composition for the oxidation dyeing of keratin fibres, and in particular human keratin fibres such as the hair, comprising, in a medium which is suitable for dyeing, at least one self-oxidizing dye, and at least one enzyme of 2-electron oxidoreductase type, in the presence of at least one donor for the said enzyme, as well as to the dyeing process using this composition.

It is known practice to dye keratin fibres, and in particular human hair, with dye compositions containing self-oxidizing dyes such as benzene derivatives comprising at least three hydroxyl and/or amino groups and indole derivatives, such as 5,6-dihydroxyindole. These self-oxidizing dyes have the particular feature of being able to be oxidized without any oxidizing agent other than atmospheric oxygen, to give rise to coloured and colouring molecules. However, the colorations obtained using these dyes are not always Satisfactory, in particular as regards their intensity and their chromaticity.

The oxidation of these self-oxidizing dyes can be promoted by using, generally in alkaline medium, a conventional oxidizing agent such as, for example, hydrogen peroxide. The use of alkaline media in the presence of hydrogen peroxide has the drawback of leading to appreciable degradation of the fibres, as well as to a bleaching of the keratin fibres which is not always desirable.

It has already been proposed to dye keratin fibres, in particular in patent application EP-A-0,310,675, with compositions comprising an oxidation dye precursor of benzene type, in combination with enzymes such as pyranose oxidase, glucose oxidase or uricase, in the presence of a donor for the said enzymes. Although being used under conditions which do not lead to a degradation of the keratin fibres comparable to that generated by the dyes prepared in the presence of hydrogen peroxide, these dyeing processes lead to colorations which are not entirely satisfactory, in particular as regards the intensity of the colorations obtained.

The Applicant has now discovered that it is possible to obtain novel dyes which, while being free of oxidation base, are capable of giving intense colorations without giving rise to significant degradation, or to any appreciable bleaching of the keratin fibres, and which are unselective and show good resistance to the various attacking factors to which the hair may be subjected, by combining at least one self-oxidizing dye and at least one enzyme of 2-electron oxidoreductase type in the presence of at least one donor for the said enzyme.

This discovery forms the basis of the present invention.

A first subject of the invention is thus a ready-to-use composition for the oxidation dyeing of keratin fibres, and in particular human keratin fibres such as the hair, characterized in that it comprises, in a medium which is suitable for dyeing:
  at least one self-oxidizing dye,
  at least one enzyme of 2-electron oxidoreductase type, and
  at least one donor for the said enzyme;
the said composition being free of oxidation base.

The ready-to-use dye composition in accordance with the invention gives intense, chromatic colorations which show low selectivity and excellent properties of resistance, both with respect to atmospheric agents such as light and bad weather, and with respect to perspiration and the various treatments to which the hair may be subjected (washing, permanent-waving operations).

A subject of the invention is also a process for the oxidation dyeing of keratin fibres using this ready-to-use dye composition.

The 2-electron oxidoreductase(s) used in the ready-to-use dye composition in accordance with the invention can be chosen in particular from pyranose oxidases, glucose oxidases, glycerol oxidases, lactate oxidases, pyruvate oxidases and uricases.

According to the invention, the 2-electron oxidoreductase is preferably chosen from uricases of animal, microbiological or biotechnological origin.

By way of example, mention may be made in particular of the uricase extracted from wild boar liver, the uricase from *Arthrobacter globiformis* and the uricase from *Aspergillus flavus*.

The 2-electron oxidoreductase(s) can be used in pure crystalline form or in a form diluted in a diluent which is inert towards the said 2-electron oxidoreductase.

The 2-electron oxidoreductase(s) in accordance with the invention preferably represent(s) from 0.01 to 20% by weight approximately relative to the total weight of the ready-to-use dye composition, and even more preferably from 0.1 to 5% by weight approximately relative to this weight.

According to the invention, the term "donor" means the various substrates which participate in the functioning of the said 2-electron oxidoreductase(s).

The nature of the donor (or substrate) for the said enzyme varies as a function of the nature of the 2-electron oxidoreductase used. For example, as donors for the pyranose oxidases, mention may be made of D-glucose, L-sorbose and D-xylose; as a donor for the glucose oxidases, mention may be made of D-glucose; as donors for the glycerol oxidases, mention may be made of glycerol and dihydroxyacetone; as donors for the lactate oxidases, mention may be made of lactic acid and its salts; as donors for the pyruvate oxidases, mention may be made of pyruvic acid and its salts; and, lastly, as donors for the uricases, mention may be made of uric acid and its salts.

The donor(s) (or substrate(s)) used in accordance with the invention preferably represent(s) from 0.01 to 20% by weight approximately relative to the total weight of the ready-to-use dye composition in accordance with the invention, and even more preferably from 0.1 to 5% approximately relative to this weight.

The nature of the self-oxidizing dye(s) used in the ready-to-use dye composition is not critical. It (they) can be chosen in particular from benzene, indole or indoline self-oxidizing dyes.

Among the benzene self-oxidizing dyes which can be used in the dye composition in accordance with the invention, mention may be made in particular of the compounds of formula (I) below, and the addition salts thereof with an acid:

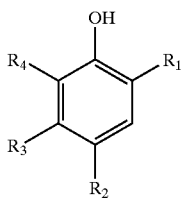

(I)

in which:

R$_1$ represents a hydrogen atom, a C$_1$–C$_4$ alkyl radical or an amino radical, R$_2$ represents a C$_1$–C$_4$ alkyl, hydroxyl, amino, mono(C$_1$–C$_4$)alkylamino or di(C$_1$–C$_4$)alkylamino radical, R$_3$ represents a hydrogen atom or a hydroxyl or amino radical, R$_4$ represents a hydrogen atom or an amino radical; it being understood that at least two of the radicals R$_1$ to R$_4$ represent, independently of each other, a hydroxyl, amino, mono(C$_1$–C$_4$)alkylamino or di(C$_1$–C$_4$) alkylamino radical.

Among the benzene self-oxidizing dyes of formula (I) above, mention may be made more particularly of 1,2,4-trihydroxybenzene, 1-methyl-2,4,5-trihydroxybenzene, 2,4-diamino-6-methylphenol, 2-amino-4-methylaminophenol, 2,5-diamino-4-methylphenol, 2,6-diamino-4-diethylaminophenol and 2,6-diamino-1,4-dihydroxybenzene, and the addition salts thereof with an acid.

Among the indole and indoline self-oxidizing dyes which can be used in the dye composition in accordance with the invention, mention may be made in particular of the compounds of formulae (II) and (III) below, and the addition salts thereof with an acid:

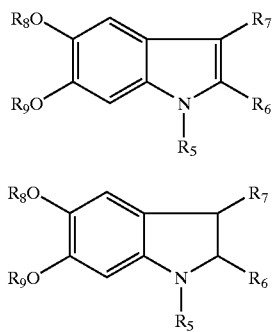

in which:

R$_5$, R$_7$, R$_8$ and R$_9$, which may be identical or different, represent a hydrogen atom or a C$_1$–C$_4$ alkyl or C$_1$–C$_4$ acyl radical, R$_6$ represents a hydrogen atom, a C$_1$–C$_4$ alkyl radical or a carboxyl radical.

Among the self-oxidizing dyes of formula (II) above, mention may be made more particularly of 5,6-dihydroxyindole, 2-methyl-5,6-dihydroxyindole, 3-methyl-5,6-dihydroxyindole, 1-methyl-5,6-dihydroxyindole, 2,3-dimethyl-5,6-dihydroxyindole, 5-methoxy-6-hydroxyindole, 5-acetoxy-6-hydroxyindole, 5,6-diacetoxyindole and 5,6-dihydroxyindole-2-carboxylic acid, and the addition salts thereof with an acid.

Among the self-oxidizing dyes of formula (III) above, mention may be made more particularly of 5,6-dihydroxyindoline, 1-methyl-5,6-dihydroxyindoline and 1-ethyl-5,6-dihydroxyindoline, and the addition salts thereof with an acid.

The self-oxidizing dye(s) preferably represent(s) from 0.0005 to 12% by weight approximately relative to the total weight of the dye composition in accordance with the invention, and even more preferably from 0.005 to 8% by weight approximately relative to this weight.

In general, the addition salts with an acid which can be used in the context of the dye compositions of the invention (self-oxidizing dyes) are chosen in particular from the hydrochlorides, hydrobromides, sulphates, tartrates, lactates and acetates.

The ready-to-use dye composition in accordance with the invention can also contain one or more direct dyes, in particular in order to modify the shades or to enrich them with glints.

The medium which is suitable for dyeing (or support) for the ready-to-use dye composition in accordance with the invention generally consists of water or a mixture of water and at least one organic solvent to dissolve the compounds which would not be sufficiently water-soluble. As organic solvents, mention may be made, for example of C$_1$–C$_4$ alkanols such as ethanol and isopropanol; glycerol; glycols and glycol ethers such as 2-butoxyethanol, propylene glycol, propylene glycol monomethyl ether, and diethylene glycol monoethyl ether and monomethyl ether, as well as aromatic alcohols such as benzyl alcohol or phenoxyethanol, similar products and mixtures thereof.

The pH of the ready-to-use composition in accordance with the invention is chosen such that the enzymatic activity of the 2-electron oxidoreductase is sufficient. It is generally approximately between 5 and 11, and preferably approximately between 6.5 and 10. It can be adjusted to the desired value using acidifying or basifying agents usually used for dyeing keratin fibres.

Among the acidifying agents, mention may be made, for example, of inorganic or organic acids such as hydrochloric acid, orthophosphoric acid, sulphuric acid, carboxylic acids such as acetic acid, tartaric acid, citric acid and lactic acid, and sulphonic acids.

Among the basifying agents, mention may be made, for example, of aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (IV) below:

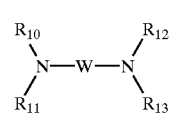

(IV)

in which W is a propylene residue optionally substituted with a hydroxyl group or a C$_1$–C$_4$ alkyl radical; R$_{10}$, R$_{11}$, R$_{12}$ and R$_{13}$, which may be identical or different, represent a hydrogen atom, a C$_1$–C$_4$ alkyl radical or a C$_1$–C$_4$ hydroxyalkyl radical.

The ready-to-use dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the 2-electron oxidoreductases used in accordance with the invention, such as, for example, peroxidases, penetrating agents, sequestering agents, fragrances, buffers, dispersing agents, conditioners such as, for example, volatile or non-volatile, modified or unmodified silicones, film-forming agents, ceramides, preserving agents and opacifiers.

Needless to say, a person skilled in the art will take care to select this (these) optional complementary compound(s) such that the advantageous properties intrinsically associated with the ready-to-use dye composition in accordance with the invention are not, or are not substantially, adversely affected by the addition(s) envisaged.

The ready-to-use dye composition in accordance with the invention can be in various forms, such as in the form of liquids, creams or gels, which may be pressurized, or in any other form which is suitable for dyeing keratin fibres, and in particular human hair. In this case, the self-oxidizing dye(s) and the 2-electron oxidoreductase(s) are present in the same ready-to-use composition, and the said composition must consequently be free of oxygen gas, so as to avoid any premature oxidation of the self-oxidizing dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is generally between 3 and 60 minutes and even more specifically between 5 and 40 minutes.

According to one specific embodiment of the invention, the process includes a first step which consists in separately storing, on the one hand, a composition (A) comprising, in a medium which is suitable for dyeing, at least one self-oxidizing dye, and, on the other hand, a composition (B) containing, in a medium which is suitable for dyeing, at least one enzyme of 2-electron oxidoreductase type, in the presence of at least one donor for the said enzyme, and then in mixing them together at the time of use, after which this mixture is applied to the keratin fibres.

Another subject of the invention is a multi-compartment dyeing device or "kit" or any other multi-compartment packaging system, a first compartment of which contains composition (A) as defined above and a second compartment of which contains composition (B) as defined above. These devices can be equipped with a means for delivering the desired mixture onto the hair, such as the devices described in patent FR-2,586,913 in the name of the Applicant.

The examples which follow are intended to illustrate the invention without, however, limiting its scope.

EXAMPLES

Dyeing Example 1 to 3

The ready-to-use dye compositions below were Prepared (contents in grams):

| COMPOSITION | 1 | 2 | 3 |
|---|---|---|---|
| 5,6-Dihydroxyindole (self-oxidizing dye) | 0.8 | — | — |
| 5,6-Dihydroxyindoline monohydrobromide (self-oxidizing dye) | — | 1.2 | — |
| 1,2,4-Trihydroxybenzene (self- | — | — | 1.0 |

-continued

| COMPOSITION | 1 | 2 | 3 |
|---|---|---|---|
| oxidizing dye) | | | |
| Uricase from *Arthrobacter globiformis* at 20 International Units (I.U./mg), sold by the company Sigma | 1.5 | 1.5 | 1.5 |
| Uric acid | 1.5 | 1.5 | 1.5 |
| Common dye support (*) | (*) | (*) | (*) |
| Demineralized water qs | 100 g | 100 g | 100 g |

(*): Common dye support:
Ethanol 20.0 g
Hydroxyethylcellulose sold under the name Natrosol 250 HR ® by the company Aqualon 1.0 g
($C_8$—$C_{10}$)alkyl polyglucoside as an aqueous solution containing 60% active material (A.M.) buffered with ammonium citrate (0.5%), sold under the name Oramix CG110 ® by the company SEPPIC 8.0 g
Monoethanolamine qs pH = 9.5

Each of the ready-to-use dye compositions described above was applied to locks of natural grey hair containing 90% white hairs, for 30 minutes. The hair was then rinsed, washed with a standard shampoo and then dried.

The hair was dyed in the shades indicated in the table below:

| EXAMPLE | Shade obtained |
|---|---|
| 1 | Ash-blonde |
| 2 | Blonde |
| 3 | Pearlescent blonde |

What is claimed is:

1. A ready-to-use composition for the oxidation dyeing of keratin fibres, comprising:
   at least one self-oxidizing dye chosen from benzene self-oxidizing dyes chosen from the compounds of formula (I) below, and the acid addition salts thereof:

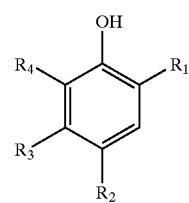

(I)

in which:
$R_1$ is chosen from a hydrogen atom, $C_1$–$C_4$ alkyl radicals, and amino radicals,
$R_2$ is chosen from $C_1$–$C_4$ alkyl, hydroxyl, amino, mono($C_1$–$C_4$)alkylamino, and di($C_1$–$C_4$) alkylamino radicals,
$R_3$ is chosen from a hydrogen atom, hydroxyl radicals, and amino radicals,
$R_4$ is chosen from a hydrogen atom and amino radicals;
wherein at least two of the radicals $R_1$ to $R_4$ independently of each other, are chosen from hydroxyl, amino, mono($C_1$–$C_4$)alkylamino, and ($C_1$–$C_4$) alkylamino radicals,
at least one enzyme chosen from 2-electron oxidoreductases, and
at least one donor for said enzyme;
wherein said composition is free of oxidation base, and wherein said at least one self-oxidizing dye is not chosen from 2,4-diaminophenol, and salts thereof.

2. A ready-to-use composition according to claim 1, wherein said 2-electron oxidoreductases are chosen from pyranose oxidases, glucose oxidases, glycerol oxidases, lactate oxidases, pyruvate oxidases, and uricases.

3. A ready-to-use composition according to claim 1, wherein said at least one enzyme is chosen from uricases of animal, microbiological, and biotechnological origin.

4. A ready-to-use composition according to claim 1, wherein said at least one enzyme is present in said composition in an amount ranging from 0.01 to 20% by weight relative to the total weight of said composition.

5. A ready-to-use composition according to claim 4, wherein said at least one enzyme is present in an amount ranging from 0.1 to 5% by weight relative to the total weight of said composition.

6. A ready-to-use composition according to claim 1, wherein said at least one donor is chosen from D-glucose, L-sorbose, D-xylose, glycerol, dihydroxyacetone, lactic acid and its salts, pyruvic acid and its salts, and uric acid and its salts.

7. A ready-to-use composition according to claim 3, wherein said at least one donor is chosen from uric acid and its salts.

8. A ready-to-use composition according to claim 7, wherein said at least one donor is present in said composition in an amount ranging from 0.01 to 20% by weight relative to the total weight of said composition.

9. A ready-to-use composition according to claim 8, wherein said at least one donor is present in an amount ranging from 0.1 to 5% by weight relative to the total weight of said composition.

10. A ready-to-use composition according to claim 1, wherein the benzene self-oxidizing dyes of formula (I) are chosen from 1,2,4-trihydroxybenzene, 1-methyl-2,4,5-trihydroxybenzene, 2,4-diamino-6-methylphenol, 2-amino-4-methylaminophenol, 2,5-diamino4-methylphenol, 2,6-diamino-4-diethylaminophenol, 2,6-diamino-1,4-dihydroxybenzene, and the acid-addition salts thereof.

11. A ready-to-use composition according to claim 1, wherein said acid-addition salts are chosen from hydrochlorides, hydrobromides, sulphates, tartrates, lactates and acetates.

12. A ready-to-use composition according to claim 1, wherein said at least one self-oxidizing dye is present in said ready-to-use composition in an amount ranging from 0.0005 to 12% by weight relative to the total weight of said ready-to-use composition.

13. A ready-to-use composition according to claim 12, wherein said at least one self-oxidizing dye is present in an amount ranging from 0.005 to 8% by weight relative to the total weight of said ready-to-use dye composition.

14. A ready-to-use composition according to claim 1, wherein
said at least one self-oxidizing dye is chosen from 1,2,4-trihydroxybenzene and acid-addition salts thereof,
said at least one enzyme is chosen from uricases, and
said at least donor is chosen from uric acid.

15. A ready-to-use composition according to claim 1, further comprising water or a mixture of water and at least one organic solvent.

16. A ready-to-use composition according to claim 1, wherein said composition has a pH ranging from 5 to 11.

17. A ready-to-use composition according to claim 1, further comprising at least one peroxidase.

18. A process for dyeing keratin fibres, comprising:
applying at least one ready-to-use dye composition to said fibres for a period of time sufficient to develop a desired coloration, wherein said ready-to-use composition comprises:
at least one self-oxidizing dye chosen from benzene self-oxidizing dyes chosen from the compounds of formula (I) below, and the acid addition salts thereof:

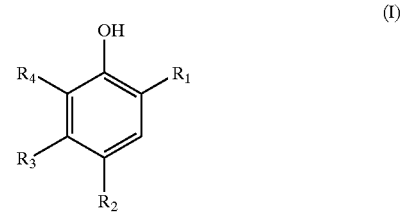

(I)

in which:
$R_1$ is chosen from a hydrogen atom, $C_1$–$C_4$ alkyl radicals and amino radicals,
$R_2$ is chosen from $C_1$–$C_4$ alkyl, hydroxyl, amino, mono($C_1$–$C_4$)alkylamino, and di($C_1$–$C_4$) alkylamino radicals,
$R_3$ is chosen from a hydrogen atom, hydroxyl radicals, and amino radicals,
$R_4$ is chosen from a hydrogen atom and amino radicals;
wherein at least two of the radicals $R_1$ to $R_4$ independently of each other, are chosen from hydroxyl, amino, mono($C_1$–$C_4$)alkylamino, and ($C_1$–$C_4$)alkylamino radicals,
at least one enzyme chosen from 2-electron oxidoreductases, and
at least one donor for said enzyme,
wherein said composition is free of oxidation base, and wherein said at least one self-oxidizing dye is not chosen from 2,4-diaminophenol, and salts thereof.

19. A process for dyeing keratin fibres, comprising:
storing a first composition separately from a second composition;
mixing said first composition with said second composition;
applying said mixture to said fibres; and,
developing for a period of time sufficient to achieve a desired coloration,
wherein said first composition comprises at least one self-oxidizing dye chosen from benzene self-oxidizing dyes chosen from the compounds of formula (I) below, and the acid addition salts thereof:

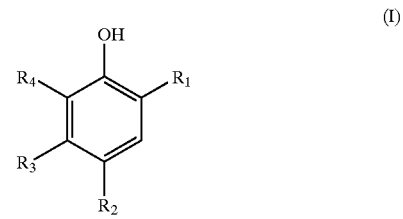

(I)

in which:
$R_1$ is chosen from a hydrogen atom, $C_1$–$C_4$ alkyl radicals, and amino radicals,
$R_2$ is chosen from $C_1$–$C_4$ alkyl, hydroxyl, amino, mono($C_1$–$C_4$)alkylamino, and di($C_1$–$C_4$) alkylamino radicals, R₃ is chosen from a hydrogen atom, hydroxyl radicals, and amino radicals, R₄ is chosen from a hydrogen atom and amino radicals;

wherein at least two of the radicals R₁ to R₄ independently of each other, are chosen from hydroxyl, amino, mono (C₁–C₄)alkylamino, and (C₁–C₄)alkylamino radicals, and said second composition comprises at least one enzyme chosen from 2-electron oxidoreductases, and at least one donor for said enzyme, and wherein both the first composition and the second composition are free of oxidation base, and wherein said at least one self-oxidizing dye is not chosen from 2,4-diaminophenol, and salts thereof.

20. A multi-compartment dyeing kit, comprising:

at least two separate compartments, wherein a first compartment contains a first composition comprising at least one self-oxidizing dye chosen from benzene self-oxidizing dyes chosen from the compounds of formula (I) below, and the acid addition salts thereof:

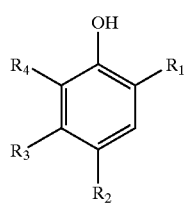

(I)

in which:

R₁ is chosen from a hydrogen atom, C₁–C₄ alkyl radicals, and amino radicals,

R₂ is chosen from C₁–C₄ alkyl, hydroxyl, amino, mono (C₁–C₄)alkylamino, and di(C₁–C₄) alkylamino radicals, R₃ is chosen from a hydrogen atom, hydroxyl radicals, and amino radicals, R₄ is chosen from a hydrogen atom and amino radicals;

wherein at least two of the radicals R₁ to R₄ independently of each other, are chosen from hydroxyl, amino, mono (C₁–C₄)alkylamino, and (C₁–C₄)alkylamino radicals, and a second compartment contains a second composition comprising at least one enzyme chosen from 2-electron oxidoreductases and at least one donor for said enzyme, wherein said first composition and said second composition are essentially free of oxidation base, wherein said first composition and said second composition are combined to form a ready-to-use dye composition, and wherein said at least one self-oxidizing dye is not chosen from 2,4-diaminophenol, and salts thereof.

21. A ready-to-use composition for the oxidation dyeing of keratin fibres, comprising:

at least one self-oxidizing dye chosen from indole and indoline self-oxidizing dyes, at least one enzyme chosen from 2-electron oxidoreductases, and at least one donor for said enzyme;

wherein said composition is free of oxidation base and peroxidase enzyme.

22. A ready-to-use composition according to claim 21, wherein said 2-electron oxidoreductases are chosen from pyranose oxidases, glucose oxidases, glycerol oxidases, lactate oxidases, pyruvate oxidases, and uricases.

23. A ready-to-use composition according to claim 21, wherein said at least one enzyme is chosen from uricases of animal, microbiological, and biotechnological origin.

24. A ready-to-use composition according to claim 21, wherein said at least one enzyme is present in said composition in an amount ranging from 0.01 to 20% by weight relative to the total weight of said composition.

25. A ready-to-use composition according to claim 24, wherein said at least one enzyme is present in an amount ranging from 0.1 to 5% by weight relative to the total weight of said composition.

26. A ready-to-use composition according to claim 21, wherein said at least one donor is chosen from D-glucose, L-sorbose, D-xylose, glycerol, dihydroxyacetone, lactic acid and its salts, pyruvic acid and its salts, and uric acid and its salts.

27. A ready-to-use composition according to claim 23, wherein said at least one donor is chosen from uric acid and its salts.

28. A ready-to-use composition according to claim 27, wherein said at least one donor is present in said composition in an amount ranging from 0.01 to 20% by weight relative to the total weight of said composition.

29. A ready-to-use composition according to claim 28, wherein said at least one donor is present in an amount ranging from 0.1 to 5% by weight relative to the total weight of said composition.

30. A ready-to-use composition according to claim 21, wherein said at least one self-oxidizing dye is present in said ready-to-use composition in an amount ranging from 0.0005 to 12% by weight relative to the total weight of said ready-to-use composition.

31. A ready-to-use composition according to claim 30, wherein said at least one self-oxidizing dye is present in an amount ranging from 0.005 to 8% by weight relative to the total weight of said ready-to-use dye composition.

32. A ready-to-use composition according to claim 21, wherein said at least one self-oxidizing dye is chosen from 5,6-dihydroxyindole, 5,6-dihydroxyindoline, and acid-addition salts thereof;

said at least one enzyme is chosen from uricases, and said at least donor is chosen from uric acid.

33. A ready-to-use composition according to claim 21, further comprising water or a mixture of water and at least one organic solvent.

34. A ready-to-use composition according to claim 21, wherein said composition has a pH ranging from 5 to 11.

35. A ready-to-use composition according to claim 21, wherein the indole and indoline self-oxidizing dyes are chosen from the compounds of formulae (II) and (III) below, and the acid-addition salts thereof:

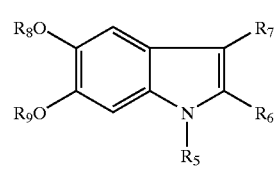

(II)

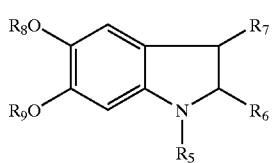

in which:

R_5, R_7, R_8 and R_9, which may be identical or different, are chosen from a hydrogen atom, $C_1$–$C_4$ alkyl radicals, and $C_1$–$C_4$ acyl radicals, R_6 is chosen from a hydrogen atom, $C_1$–$C_4$ alkyl radicals, and carboxyl radicals.

36. A ready-to-use composition according to claims 35, wherein the self-oxidizing dyes of formula (II) are chosen from 5,6-dihydroxyindole, 2-methyl-5,6-dihydroxyindole, 3-methyl-5,6-dihydroxyindole, 1-methyl-5,6-dihydroxyindole, 2,3-dimethyl-5,6-dihydroxyindole, 5-methoxy-6-hydroxyindole, 5-acetoxy-6-hydroxyindole, 5,6-diacetoxyindole, 5,6-dihydroxyindole-2-carboxylic acid, and the acid-addition salts thereof.

37. A ready-to-use composition according to claim 35, wherein the self-oxidizing dyes of formula (III) are chosen from 5,6-dihydroxyindoline, 1-methyl-5,6-dihydroxyindoline, 1-ethyl-5,6-dihydroxyindoline, and the acid-addition salts thereof.

38. A ready-to-use composition according to claim 35, wherein said acid-addition salts are chosen from hydrochlorides, hydrobromides, sulphates, tartrates, lactates and acetates.

39. A process for dyeing keratin fibres, comprising:
applying at least one ready-to-use dye composition to said fibres for a period of time sufficient to develop a desired coloration, wherein said ready-to-use composition comprises:
at least one self-oxidizing dye chosen from indole and indoline self-oxidizing dyes,
at least one enzyme chosen from 2-electron oxidoreductases, and
at least one donor for said enzyme, wherein said composition is free of oxidation base and peroxidase enzyme.

40. A process for dyeing keratin fibres, comprising:
storing a first composition separately from a second composition;
mixing said first composition with said second composition;
applying said mixture to said fibres; and,
developing for a period of time sufficient to achieve a desired coloration,
wherein said first composition comprises at least one self-oxidizing dye chosen from indole and indoline self-oxidizing dyes, and said second composition comprises at least one enzyme chosen from 2-electron oxidoreductases, and at least one donor for said enzyme, and wherein both the first composition and the second composition are free of oxidation base and peroxidase enzyme.

41. A multi-compartment dyeing kit, comprising:
at least two separate compartments, wherein a first compartment contains a first composition comprising at least one self-oxidizing dye chosen from indole and indoline self-oxidizing dyes, and a second compartment contains a second composition comprising at least one enzyme chosen from 2-electron oxidoreductases and at least one donor for said enzyme, wherein said first composition and said second composition are free of oxidation base and peroxidase enzyme and wherein said first composition and said second composition are combined to form a ready-to-use dye composition.

* * * * *

UNITED STATES PATENT AND TRADEMARK OFFICE
CERTIFICATE OF CORRECTION

PATENT NO.     : 6,423,100 B1
DATED          : July 23, 2002
INVENTOR(S)    : Gérard Lang et al.

It is certified that error appears in the above-identified patent and that said Letters Patent is hereby corrected as shown below:

Title page,
Item [57], ABSTRACT,
Line 5, after "oxidoreductase" delete the comma;

Column 6,
Lines 63 and 64, "and ($C_1$-$C_4$)alkylamino" should read -- and di($C_1$-$C_4$)alkylamino --;

Column 7,
Line 39, "2,5-diamino4-methylphenol" should read -- 2,5-diamino-4-methylphenol --;

Column 8,
Line 21, after "radicals" insert a comma;
Line 32, "($C_1$-$C_4$)alkylamino" should read -- di($C_1$-$C_4$)alkylamino --;

Column 9,
Lines 43 and 47, "and ($C_1$-$C_4$)alkylamino" should read -- and di($C_1$-$C_4$)alkylamino --;

Column 10,
Line 46, "thereof;" should read -- thereof, --; and
Line 57, "(I11)" should read -- (III) --.

Signed and Sealed this

Twenty-sixth Day of November, 2002

*Attest:*

JAMES E. ROGAN
*Attesting Officer*    *Director of the United States Patent and Trademark Office*